United States Patent
Nimtsovitch

(10) Patent No.: US 10,376,439 B2
(45) Date of Patent: Aug. 13, 2019

(54) AUDIO-FEEDBACK COMPUTERIZED SYSTEM AND METHOD FOR OPERATOR-CONTROLLED EYE EXERCISE

(71) Applicant: DIPLO D LTD., Netanya (IL)

(72) Inventor: Claude Nimtsovitch, Netanya (IL)

(73) Assignee: DIPLO D LTD., Netanya (IL)

( * ) Notice: Subject to any disclaimer, the term of this patent is extended or adjusted under 35 U.S.C. 154(b) by 917 days.

(21) Appl. No.: 14/896,682

(22) PCT Filed: Jun. 10, 2014

(86) PCT No.: PCT/IL2014/000031
§ 371 (c)(1),
(2) Date: Dec. 8, 2015

(87) PCT Pub. No.: WO2014/199366
PCT Pub. Date: Dec. 18, 2014

(65) Prior Publication Data
US 2016/0128892 A1 May 12, 2016

(30) Foreign Application Priority Data

Jun. 11, 2013 (IL) .......................................... 226878

(51) Int. Cl.
*A61H 5/00* (2006.01)
*A61B 3/113* (2006.01)

(52) U.S. Cl.
CPC ................ *A61H 5/00* (2013.01); *A61B 3/113* (2013.01); *A61H 2201/5007* (2013.01); *A61H 2201/5023* (2013.01); *A61H 2205/024* (2013.01)

(58) Field of Classification Search
CPC ........................................................ A61H 5/00
See application file for complete search history.

(56) References Cited

U.S. PATENT DOCUMENTS

| | | | | |
|---|---|---|---|---|
| 1,972,624 | A * | 9/1934 | Hendrick | A61H 5/00 351/203 |
| 2,263,190 | A * | 11/1941 | Quinan | A61H 5/00 351/203 |
| 5,422,688 | A * | 6/1995 | Asea | A61H 5/00 351/203 |
| 8,595,949 | B2 * | 12/2013 | Reichow | A61H 5/00 33/511 |
| 2001/0050754 | A1 | 12/2001 | Hay et al. | |

(Continued)

FOREIGN PATENT DOCUMENTS

| | | | |
|---|---|---|---|
| IL | 119274 | 12/2000 | |
| WO | WO-9811819 A1 * | 3/1998 | ............... A61H 5/00 |

(Continued)

*Primary Examiner* — Charlie Y Peng
(74) *Attorney, Agent, or Firm* — Alphapatent Associates, Ltd; Daniel J. Swirsky

(57) ABSTRACT

The present invention provides a computerized operator-controlled optical system and method for tracking eye exercises of a patient, the system including an optical tracking device adapted to allow an operator to track eye exercises of a patient, a patient-activated apparatus for performing eye exercises of binocular vision and a processor adapted to receive data from the optical tracking device and from the patient-activated apparatus thereby providing the operator with at least one indication of the eye exercises of said patient over time.

11 Claims, 10 Drawing Sheets

(56) References Cited

U.S. PATENT DOCUMENTS

| | | | |
|---|---|---|---|
| 2006/0087618 A1* | 4/2006 | Smart | A61B 3/005 |
| | | | 351/222 |
| 2006/0164597 A1 | 7/2006 | Hayakawa et al. | |
| 2007/0200927 A1 | 8/2007 | Krenik et al. | |
| 2010/0283969 A1 | 11/2010 | Cooperstock et al. | |

FOREIGN PATENT DOCUMENTS

| WO | 2012135822 A2 | 10/2002 |
|---|---|---|
| WO | 2009138964 A2 | 11/2009 |
| WO | 2010102037 A2 | 9/2010 |
| WO | 2013076211 A1 | 5/2013 |

* cited by examiner

Diplo-D Software v.1.005

File  Patient  Tools  Help

Patient | Tests | Statistics | Control

Patient Test History:

First Name: [____]  Second Name: [____]  Date of Test: [____] ▽△

Patient Test History:

Phoria for near: 802    CNP: 804    Worth 4 dots: 806

Abduction for near D': 816   Titmus sterioscopic vision: 808   810

Speed: 814    Adduction for near C': 818    Symptoms: 820
                                              OC/GL  OS/GL
                    Last Treatment Level: 816 ▽

○ Test before treatment    840  842
                                              ○ Test after treatment     Save  Clear
                                                    830

Select patient on first page.

USB Status:OFF | Serial Port OFF    Mode: Doctor | 12/02/2013 | 15:27

AUDIO-FEEDBACK COMPUTERIZED SYSTEM AND METHOD FOR OPERATOR-CONTROLLED EYE EXERCISE

CROSS-REFERENCE TO RELATED APPLICATIONS

This application is a U.S. National Phase Application under 35 U.S.C. 371 of International Application No. PCT/IL2014/000031, which has an international filing date of Jun. 10, 2014, and which claims the benefit of priority of Israel Patent Application No. 226,878, filed Jun. 11, 2013, the disclosures of which are incorporated herein by reference in their entirety.

FIELD OF THE INVENTION

The present invention relates generally to systems and methods for improving eye activities, and more specifically to computerized operator-controlled methods and apparatus for improving eye activities.

BACKGROUND OF THE INVENTION

Many prior art devices have been developed to assist a person with eye focus defects to perform orthoptic eye exercises. These exercises are adapted to correct mainly fusion deficiencies, such as, but not limited to convergence insufficiency, divergence excess or intermittent strabismus. Convergence insufficiencies include exophoria or esophoria. Intermittent strabismus includes intermittent exotropia and esotropia.

These prior systems currently in use are based on the stereoscopic effect or binocular vision, wherein each eye is presented a separate picture, and the patient is required to exert the eyes muscles to integrate the two pictures into one focused image.

Moreover, these prior art devices are not useful for the intermittent suppression deficiency, that is while one eye ceases at times from participating in the image forming process. When this happens, the usual eye exercises are no more effective.

In prior art Israel Patent No. 119274, the present inventor disclosed a device which can be used at home. However, the picture movement is made manually by the user himself. Sometimes the velocity of movement is not appropriate for the desired exercise. There may not be sufficient consistency in the exercise, when performing it at a different rate each time.

Moreover, the user has no indication, while performing the exercise, of the actual performance having been achieved. Only after finishing the exercise, the user can look at the achieved performance; this may not be enough an incentive for improvement, nor does it give an intuitive feeling for what is done, in real time.

Yet another possible problem in prior art is that the user is responsible for deciding when picture tracking is lost—this is important in evaluating the success of the exercise, as well as motivating the user.

However, the non-professional user may not be aware of his losing track, or may become aware of it only after a time delay—thus the effectiveness of the device may be impaired.

WO2009/138964 to Nimkovitch describes an optical apparatus for performing eye exercise comprising base means shaped generally like an elongated beam; picture means which is suitable for eye exercise and includes positioning means for positioning said picture means at various locations along said base means; electrical light means attached to said base means, including lamp means and switch means for turning said lamp on and off; ocular means including two viewing apertures, each located in front of one eye, said ocular means being mounted on or close to one end of said base means; audio feedback means for generating, during the eye exercise performance, an audio signal whose characteristics are indicative of the distance of the moving picture from the user's eyes.

None of the prior art devices allow a professional operator, such as an optician, a physician or a technician to track the user or patient's progress and to compare his/her progress over time. There thus remains a need to provide improved othorptic devices and methods.

SUMMARY OF THE INVENTION

It is an object of some aspects of the present invention to provide a computerized operator-controlled optical system and method for tracking eye exercises of a patient, the system including an optical tracking device adapted to allow an operator to track eye exercises of a patient, a patient-activated apparatus for performing eye exercises of both eyes together and a processor adapted to receive data from the optical tracking device and from the patient-activated apparatus thereby providing the operator with at least one indication of the eye exercises of said patient over time.

This invention relates to orthoptic eye exercise devices having two fixation centers and using audio feedback.

According to the present invention, there is provided an optical device for performing orthoptic eye exercise at patient's home.

According to one aspect of the present invention, the device includes two fixation centers, each located on the axis of symmetry between the eyes, each center including a picture used for eye exercise.

The patient can choose to look at one picture at a time, with the other picture appearing double.

The two pictures are replaceable, with a different picture pair being used each time, as necessary. The eye exercise device includes a trial frame, whose distance between the two eyes is adjustable, with replaceable optical accessories. The replaceable optical accessories may include lenses and/or prisms.

The distance to the closer fixation center and its picture is adjustable. The eye exercise device includes two lights, each included in one fixation center, with means for the activation of each light. According to a seventh aspect of the present invention, the device further includes colored filters for eye exercise purposes.

Furthermore, the invention includes automatic means for moving the closer picture toward the user's eyes at a controlled velocity, to achieve a consistent framework for exercising.

The invention also includes audio feedback means for indicating to the user, in real time, the measure of closeness of the picture to the eyes, that is the index of user's achievement in the present exercise.

Moreover, the eyes tracking performance may be automatically measured and loss of tracking may be automatically detected, to achieve a more reliable indice than when relying on user's judgment.

The structure of the device is modular, with the user having a choice of either a simple, low cost device or a more advanced system offering more benefits.

Further objects, advantages and other features of the present invention will become obvious to those skilled in the art upon reading the disclosure set forth hereinafter.

There is thus provided according to an embodiment of the present invention, a computerized operator-controlled optical system for tracking eye exercises of a patient, the system including;
 a. an optical tracking device adapted to allow an operator to track eye exercises of a patient;
 b. a patient-activated apparatus for performing eye exercises of two eyes together; and
 c. a processor adapted to receive data from the optical tracking device and from the patient-activated apparatus thereby providing the operator with at least one indication of the eye exercises of the patient over time.

Additionally, according to an embodiment of the present invention, the computerized operator-controlled optical system further includes an electronic apparatus adapted to download the data to a memory in the system.

Furthermore, according to an embodiment of the present invention, the computerized operator-controlled optical system further includes software readable by the processor, wherein the software is adapted to form patient records over time.

Moreover, according to an embodiment of the present invention, the optical tracking device is a camera.

Additionally, according to an embodiment of the present invention, the optical tracking device is a video camera.

Further, according to an embodiment of the present invention, the camera is adapted to capture images of each the patient's eyes of several times second.

Moreover, according to an embodiment of the present invention, the software is adapted to output patient records to an external computer system.

Additionally, according to an embodiment of the present invention, the system is constructed and configured to improve eye fusion deficiencies of the patient over time.

Furthermore, according to an embodiment of the present invention, the fusion deficiencies, are selected from convergence insufficiency, divergence excess, intermittent strabismus and combinations thereof.

Additionally, according to an embodiment of the present invention, the convergence insufficiencies are selected from exophoria and intermittent exotropia.

Moreover, according to an embodiment of the present invention, the intermittent strabismus is intermittent exotropia.

Additionally, according to an embodiment of the present invention, the patient-activated apparatus includes;
 a. an ocular apparatus including;
  i. two viewing apertures, each disposed to be located in front of one of the patient's eye;
  ii. each of the viewing apertures adapted to receive at least one of;
   a. an optical lens (plus, minus lens, or cylinder lenses);
   b. a color filter;
   c. a Polaroid lens adapted to be placed in front of each eye;
   d. an optical prism; and
   e. an optical filter.

Furthermore, according to an embodiment of the present invention, the patient-activated apparatus further includes;
 a. a carrier element adapted to carry at least two test images towards and away from the ocular apparatus.

Additionally, according to an embodiment of the present invention, the test images includes at least one of a picture, a photo, an alphanumeric symbol, a three dimensional (3D) item and at least one red colored shape.

Furthermore, according to an embodiment of the present invention, the patient-activated apparatus further includes;
 b. at least one electrical light element attached to the carrier element; and
 c. a computerized operator-controlled optical system wherein the at least one electrical light element each includes a lamp means and switch means for turning the lamp on and off.

Moreover, according to an embodiment of the present invention, the patient-activated apparatus further includes an audio feedback element for generating, during the eye exercises, an audio signal whose characteristics are indicative of a distance of one of the at least two test images from the viewing apertures.

Additionally, according to an embodiment of the present invention, the carrier element further includes a distance adjusting element adapted to position the at least two images and the lamp means each at an equal distance from the two viewing apertures.

Yet further, according to an embodiment of the present invention, A computerized operator-controlled optical system further including a remote controlled motor for moving the image towards the two viewing apertures.

Additionally, according to an embodiment of the present invention, the audio feedback signal's characteristics include its frequency.

Further, according to an embodiment of the present invention, the audio feedback signal includes pulses and the signal's characteristics include its pulse repetition rate.

Furthermore, according to an embodiment of the present invention, the signal's characteristics further include the signal's frequency.

There is thus provided according to an additional embodiment of the present invention, a computerized operator-controlled optical method for tracking eye exercises of a patient, the method including;
 a. performing eye exercises of both the patient's eyes together to form a patient data output;
 b. operator controlled tracking of the eye exercises of the patient to form an operator data output; and
 c. processing the patient data output and the operator data output over time thereby providing the operator with at least one indication of the eye exercises of the patient over time.

Additionally, according to an embodiment of the present invention, the computerized operator-controlled optical method further includes storing the patient data output and the operator data output over time in at least one of a computer memory and a memory card.

Moreover, according to an embodiment of the present invention, the computerized operator-controlled optical method further includes tracking a reduction in eye fusion deficiencies of the patient over time.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 8 is another simplified screen shot of a patient tracking record in the system of FIG. 1, in accordance with an embodiment of the present invention;

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1:
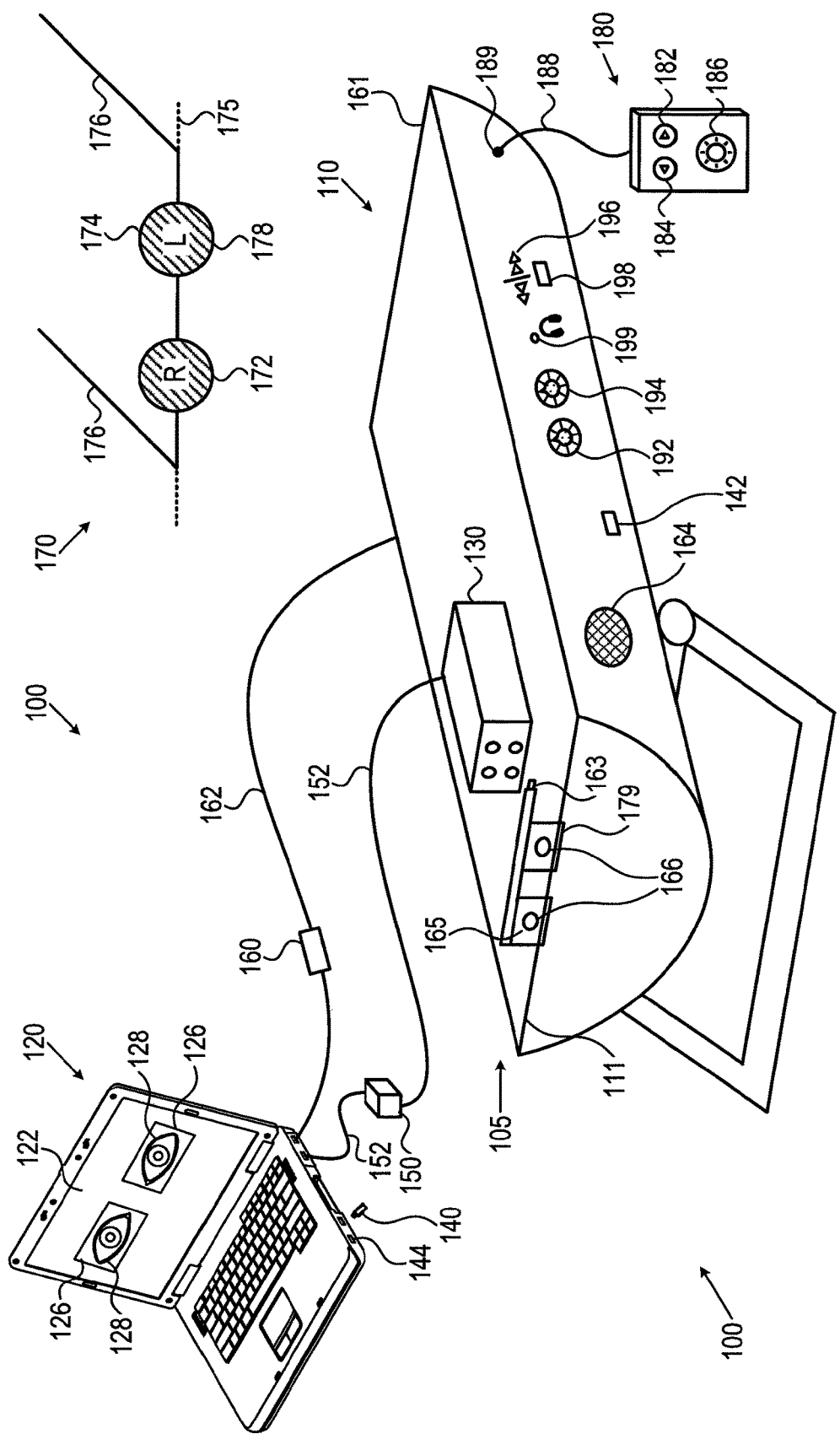
FIG. 1 is a simplified schematic illustration showing a system for computerized operator-controlled optical system for tracking eye exercises of a patient, in accordance with an embodiment of the present invention.

Reference is now made to FIG. 1, which is a simplified schematic illustration showing a system 100 for computerized operator-controlled optical system for tracking eye exercises of a patient, in accordance with an embodiment of the present invention.

System 100 comprises an apparatus (also termed device herein) 110 for computerized operator-guided for tracking eye exercises of the patient. The apparatus comprises an optical tracking device 130, such as a video camera, which is constructed and configured to enable an operator to track eye exercises of a patient. Additionally, the apparatus comprises a user-operated control 180 for activating apparatus 110. The optical tracking device 130 may include, according to some embodiments night vision means ((not shown) such as an ITU gaze tracker as exemplified in: San Agustin, J., Skovsgaard, H., Mollenbach, E., Barret, M., Tall, M., Hansen, D. W., and Hansen, J. P. 2010. *Evaluation of a low-cost open-source gaze tracker*. In *Proceedings of the 2010 Symposium on Eye-Tracking Research & Applications* (Austin, Tex., Mar. 22-24, 2010). ETRA '10. ACM, New York, N.Y., 77-80. DOI=http://doi.acm.org/10.1145/1743666.1743685). Additionally or alternatively, the optical tracking device 130 may further include an infrared light (not shown).

Apparatus 110 comprises an eyepiece apparatus 106 for receiving one or more lenses 165, 179 into two receiving elements 166. The eyepiece apparatus further comprises an adjusting element 162 for adjusting the distance between the two receiving elements. Adjusting element 162 may be manual or electronic, as is known in the art. The lenses may be suited to the user's eyesight. They may be optic lenses with or without a cylinder, as will be explained in further detail herein below.

Additionally or alternatively, a color filter lens 172 and a color filter lens 174 may be added into two receiving elements 166.

Additionally or alternatively, the user or patient may wear eyeglasses 170. Eyeglasses 170 comprise a red color filter lens 172 and a green color filter lens 174 and two temples 176. The eyeglasses are symmetric about a horizontal axis 175 and may be turned over such that they can first be used as shown in the drawing (FIG. 1) with the green lens on the left eye and the red lens on the right eye. Thereafter, they can be used with the red lens on the left eye and the green lens on the right eye. The lenses are typically housed in a fixed frame, although, according to some embodiments, the frame may be adjustable.

The user-operated control 180 comprises a forward button 182 for moving a near frame 310 (FIG. 3) towards a front end 111 of the apparatus and a reverse button 184 for moving the near frame towards a rear end 161 of the apparatus. Depression of either button a second time stops the movement end of the near frame. Additionally, there is a light select button 186 for activating a light (316, FIG. 3) on/off. The user-operated control 180 is typically in wired connection 188 with the apparatus. Typically, lights 196, 198, such as green light is activated indicative of forward movement, a yellow light indicative of backward movement and a red light at both ends of the device when movement of the frame movement stops. If the movement is stopped before the end of the device, the red light may be a red flashing light.

When the near frame is moving backwards, the patient is asked to stare on the rear frame and a taped vocal tape is activated. One non-limiting example of the taped message is "NOW RELAX. BLINKING GENTLY AND SMOOTHLY AND STARING FREELY. TURN YOUR EYES FROM SIDE TO SIDE, THEN IN A COMPLETE CIRCLE FROM LEFT TO RIGHT, AND BACKWARDS. LET YOUR EYES MUSCLES RELAX COMPLETELY!" This message may be played with background music or a short story.

When the near frame is moving forwards, a sound track is provided with sounds of increasing frequency and pitch, proportional to the stage or step of forward movement of the frame. The sound track changes with the movement of the near frame (little picture) towards the patient's eyes and concurrently the sound increases frequency. The pitch at each "step" or "stage" of the sound track increases stage-wise, for example with the performance of the patient. However, the sound track frequency and pitch does not changes with the speed of the movement of the near frame.

Additionally, the apparatus comprises an adjustable speed control 192 and an adjustable volume control 194. The apparatus typically comprises a port 198 for speakers, and other electronic connections, such as a headphone port 198 and speakers' port 199.

According to some embodiments, the apparatus is used in conjunction with a computer 120, which adapted to receive data from the optical tracking device and from said patient-activated apparatus thereby providing said operator with at least one indication of said eye exercises of said patient over time.

According to some embodiments, several apparatus units 110 can be connected to computer 120, whose screen 122 may be suitably divided into several parts. Such a system may be used in an orthoptic treatment center in which several patients are undergoing treatment simultaneously.

The computer is in wired connection 152 with the camera. The connection may be activated by a switch 150.

Additionally, apparatus 110 is in wired connection 163 to the computer. The connection may be activated by a switch 169. The apparatus further comprises a port 142 for a memory card 140, which can also be introduced to port 144 on the computer.

Figure 2:
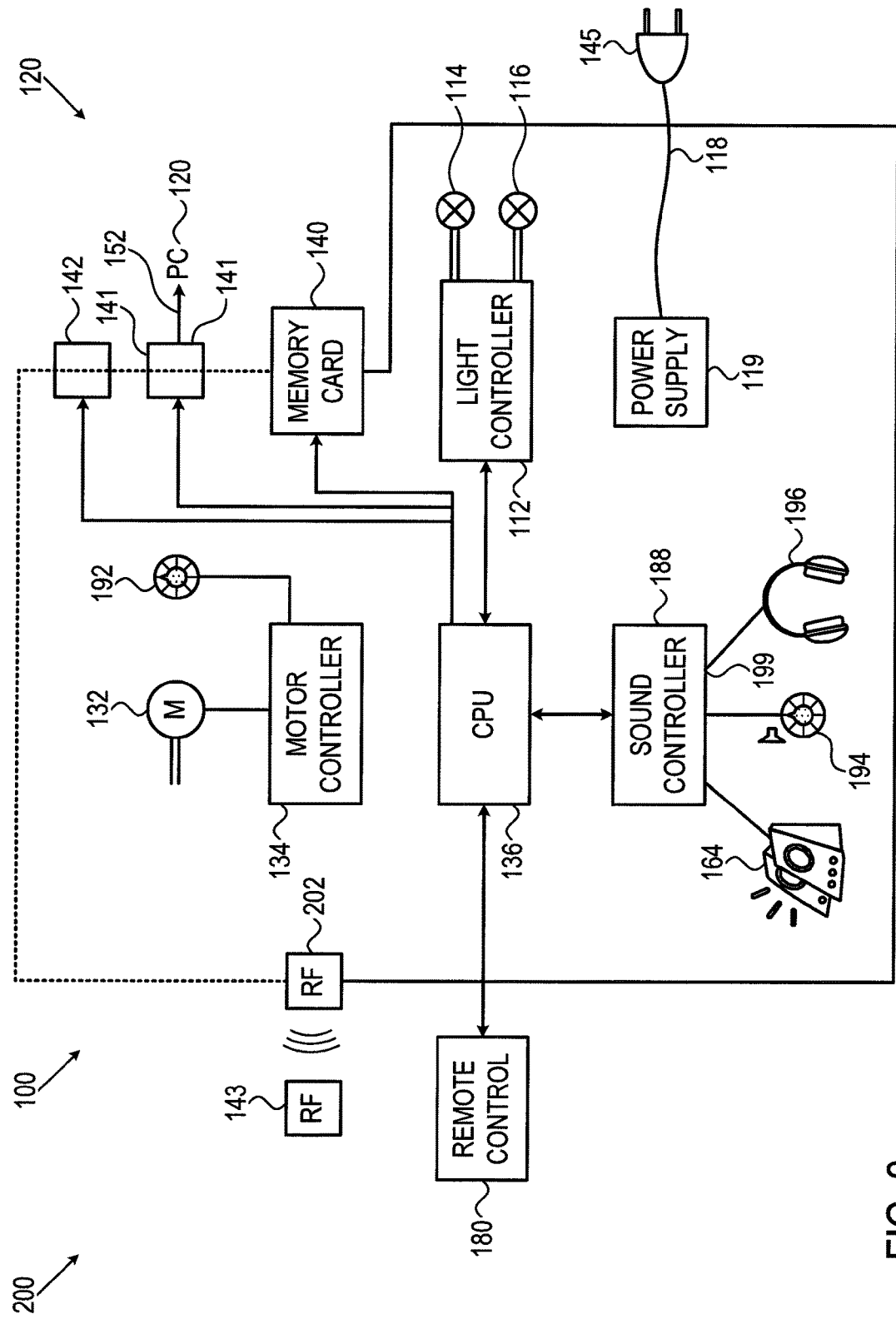
FIG. 2 is a simplified block diagram showing an apparatus for computerized operator-controlled optical system for tracking eye exercises of a patient, in accordance with an embodiment of the present invention.

Reference is now made to FIG. 2, which is a simplified block diagram showing an apparatus 110 for computerized operator-controlled optical system for tracking eye exercises of a patient, in accordance with an embodiment of the present invention.

Apparatus 110 comprises an RF receiver 202, which is in communication with an RF communication system 143. The apparatus is activated by the remote control 180. A central processing unit 136 is operative to send signals to a light controller 112. The light controller is in wired communication with a static lamp 114 and a moving lamp 116. The apparatus is activated by mains electricity via an electrical lead 118 and a plug 145, to a power supply (not shown). This may be 110V to 240 V and 50-60 Hz. The power supply provides electricity at the correct voltage/amperage to each of the units and controllers in the apparatus.

A sound controller 188 is connected to the CPU and to the adjustable volume control 194, as well as to apparatus speakers 164 and to external headphones via headphone port 199. The apparatus is constructed and configured to enable recording of a new voice message by depressing a "record" button (not shown) simultaneously, as is known in the art.

Additionally, the lights 305, 314 may be switched on/off or dimmed, as is known in the art.

Figure 3:
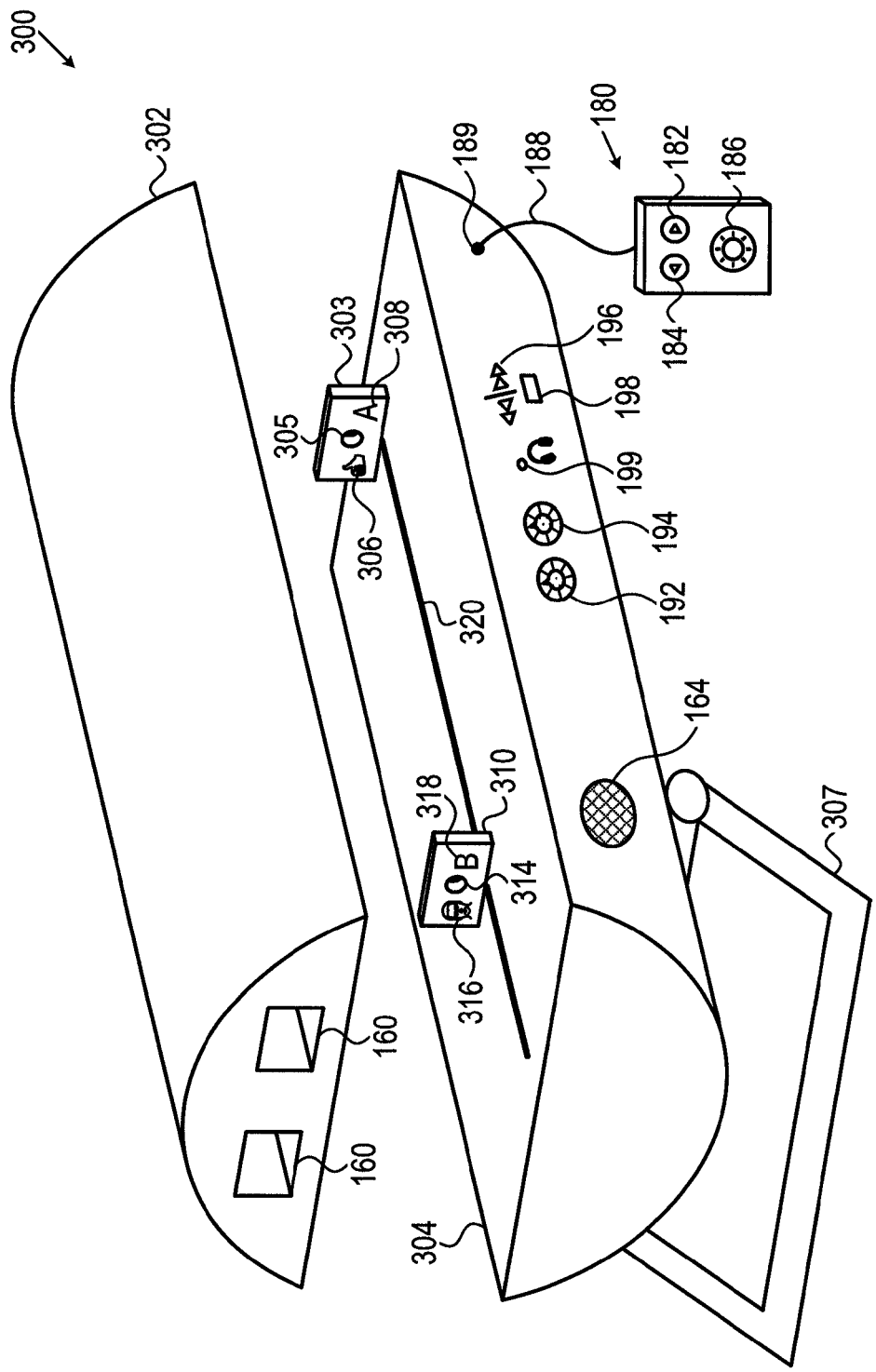
FIG. 3 is a simplified diagram three dimensional illustration of the apparatus of FIG. 2; in accordance with an embodiment of the present invention.

A motor 132 is controlled by a motor controller 134, which is connected to the adjustable speed control 192. The motor is constructed and configured to move near frame 310 along a rail 320 (FIG. 3). The speed is typically in the range of 1.5 to 5 cm/second (movement of 35 cm in 8-20 seconds).

The CPU also is in communication with memory card 140.

Turning to FIG. 3, there can be seen is a simplified three dimensional illustration 300 of the apparatus of FIG. 2; in accordance with an embodiment of the present invention.

The apparatus comprises a lid 302 and a base 304. The base comprises a support 307 adapted to raise at least part of the apparatus above a flat surface, such as a table.

The apparatus comprises near frame 310, which is mounted vertically on the horizontal rail, which runs along much of the length of the apparatus.

The near frame comprises a centrally placed lamp/light 314, a first picture 316 and a first alphanumeric character 318.

The rear frame 303 comprises a centrally placed lamp/light 305, a second picture 306 and a second alphanumeric character 308. The second picture is larger than the first picture, typically about 150% as large.

According to some embodiments, the first alphanumeric character 318 is red and second alphanumeric character 308 is red.

Figure 4:
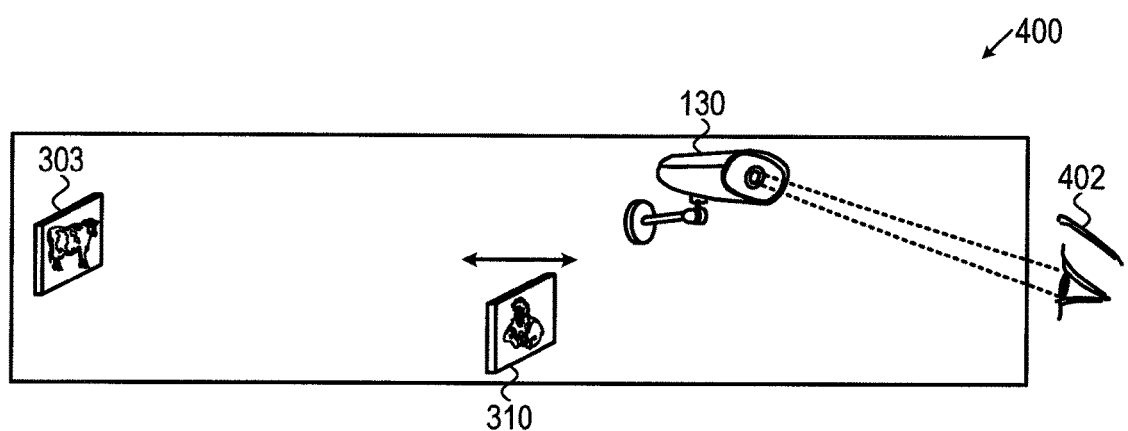
FIG. 4 is a simplified vertical cross section of the apparatus of FIG. 2, in accordance with an embodiment of the present invention.

Reference is now made to FIG. 4, which is a simplified vertical cross section 500 of the apparatus of FIG. 2, in accordance with an embodiment of the present invention.

Camera 130 tracks the movement of the eyes 402 of the patient. In some cases, the camera relays a real-time image of the eyes to computer 120 (FIG. 1). The user uses the remote control and speed controller to move the near frame 310 backwards and forwards relative to the far frame and the camera monitors changes in the eye position, pupil position of both eyes of the user (see FIGS. 5A and 5B).

Figure 5A:
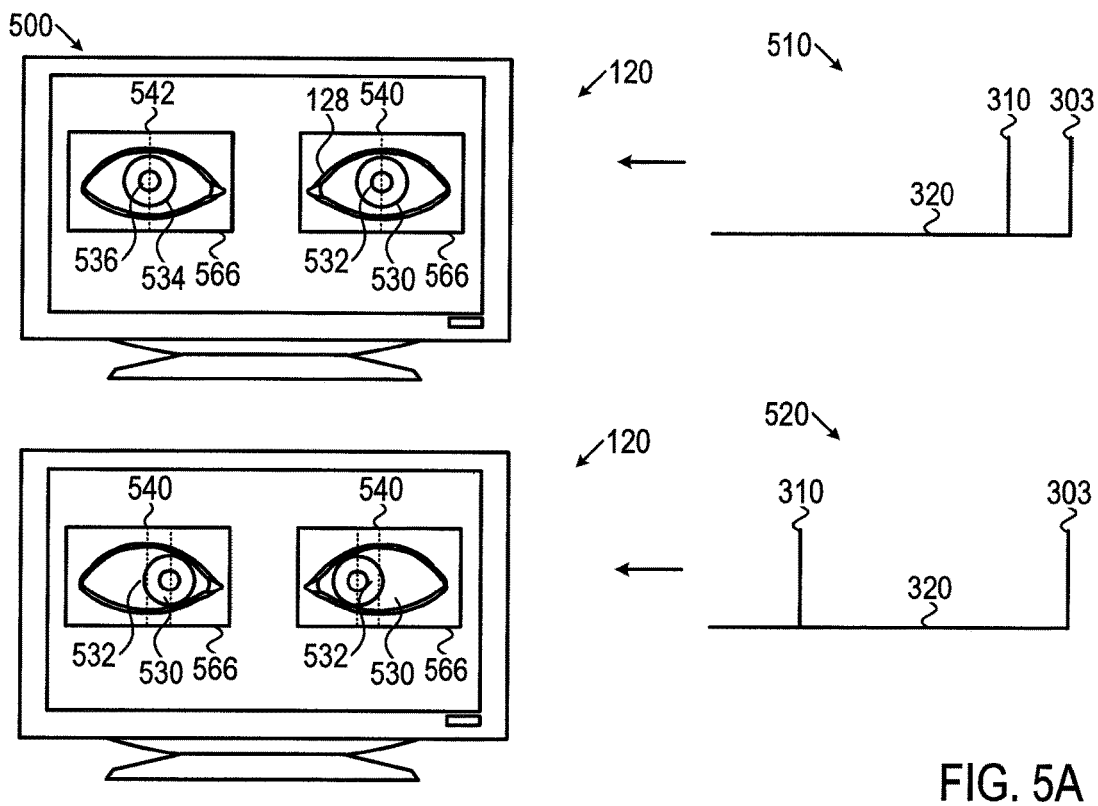
FIG. 5A is a schematic illustration of the apparatus of FIG. 2 in two positions and eye convergence of a first patient, in accordance with an embodiment of the present invention.

Reference is now made to FIG. 5A, which is a schematic illustration 500 of the apparatus of FIG. 2 in two positions 510, 520 and eye convergence of a first patient, in accordance with an embodiment of the present invention.

When near frame 310 is in a first position 510 proximal to far frame 303; the image of the patients eyes 128 appear on screen 122 of computer 120. The eyes can be seen inside an image of the inside of images 566 of two receiving elements 166 (FIG. 1). The pupils 532, 536 appear inside irises 530, 534 of the eyes. When the eyes are focused on the near frame 310, the pupils appear to be central along two vertical central axes 540, 542 respectively.

The patient then moves the near frame to the second position 520, near to the front end of the apparatus. Now the patient's eyes converge inwardly to a new position along vertical axes 544 and 546, which are nearer to each other than axes 540 and 542. In a healthy person, the eyes will move symmetrically.

Figure 5B:
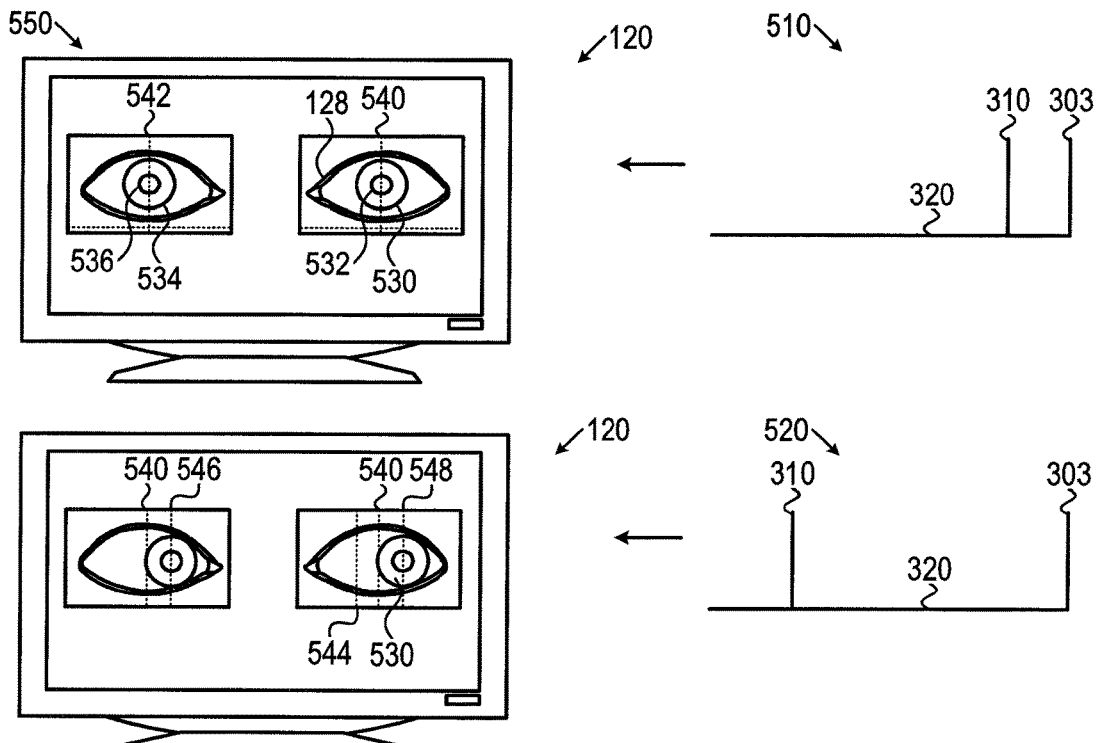
FIG. 5B is a schematic illustration of the apparatus of FIG. 2 in two positions and one eye convergence and one eye divergence of a second patient, in accordance with an embodiment of the present invention.

FIG. 5B is a schematic illustration 550 of the apparatus of FIG. 2 in two positions and one eye convergence and one eye divergence of a second patient, in accordance with an embodiment of the present invention.

When near frame 310 is in a first position 510 proximal to far frame 303; the image of the patients eyes 128 appear on screen 126 of computer 120. The eyes can be seen inside an image of the inside of images 566 of two receiving elements 166 (FIG. 1). The pupils 532, 536 appear inside irises 530, 534 of the eyes. When the eyes are focused on the near frame 310, the pupils appear to be central along two vertical central axes 540, 542 respectively.

The patient then moves the near frame to the second position 520, near to the front end of the apparatus. Now one of the patient's eyes converges inwardly to a new position along vertical axes 544 and 546, which is nearer to axes 540 than is axis 542. In this second patient, the second eye diverges to a new position along a third vertical axis 548, which is further away from axis 542 than is axis 540.

The second patient needs to undergo several sessions of eye training using system 100 of FIG. 1.

Figure 6:
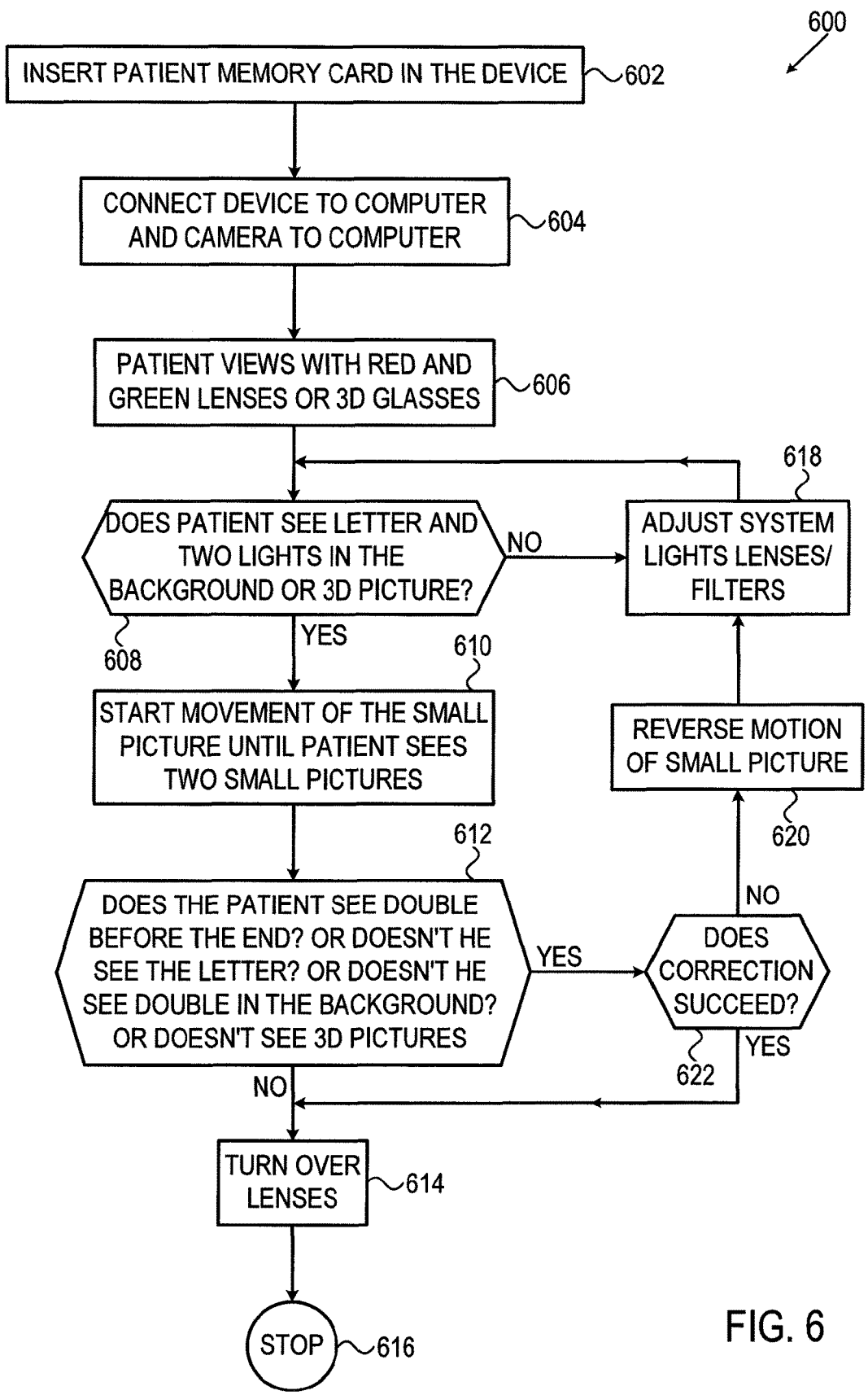
FIG. 6 is a simplified flowchart of a computerized operator-controlled method for tracking eye exercises of a patient, in accordance with an embodiment of the present invention.

Reference is now made to FIG. 6, which is a simplified flowchart of a computerized operator-controlled method 600 for tracking eye exercises of a patient, in accordance with an embodiment of the present invention.

In an insertion step 602, the patient's memory card 140 is inserted into port 144/142 of the device (or apparatus, FIG. 1).

The computer is connected to apparatus 110 and the camera 130 is connected to the computer in a connecting step 604.

The patient puts on, for example, the red and green glasses 170 or alternatively red and green lenses are mounted in the receiving elements 166 (FIG. 1) and the patient views the near and far frames via eyepiece 160 in a viewing step 606 and the near frame 310 is moved towards the patient's eyes on the rail/axis until the patient sees two pictures.

In a checking step 608, the operator checks to see if the patient can see alphanumeric symbols (letters) 318 and 308 or red printed image, and two lights in the background.

If yes, then movement of the small frame including the small picture is moved until the patient sees two small pictures, in a moving small frame step 610.

If no, then in an adjusting step 618, the operator adjust system lights, lenses and filters as may be required to suit the patient's current eye status and/or in accordance with the stages described in Table 2 herein below. Thereafter, steps 608-612 are repeated.

In a second checking step 612, the operator checks to see if the patient sees double before the small frame has reached the end of the track. Additionally or alternatively, the operator checks to see if the patient sees the letter, number or red symbol. Additionally or alternatively, the operator checks to see if the patient sees double in the background. Then, the red and green lens positions over right and left eyes are swapped and/or the glasses are turned over in a turning/swapping step 614. Thereafter, steps 608-614 may be repeated.

If yes, the operator may stop the motion of the small frame and try to correct in a correcting step 622. This step may be repeated until a correction is achieved. If the correction is successful, then step 614 is performed. If no, then the operator reverses the motion of the small frame in a reversing motion step 620. Thereafter, steps 608-614 are repeated.

The steps of the present methodology may be repeated a number of times in one eye training session. The patient may undergo several training sessions over a number of weeks or months until at least some of the parameters defined in table 1 have improved qualitatively/quantitatively.

Additionally or alternatively, the steps of the present methodology may be repeated a number of times in one eye training session. The patient may undergo several training sessions over a number of weeks or months until the convergence insufficiency, as seen in FIG. 5B has been corrected, at least in part, to that of FIG. 5A.

System 100 of FIG. 1 comprises double control of the binocular vision that is by:
1) Color glasses 170 (seeing or not the red symbol or alphanumeric character) or by Polaroid glassed (not shown)
2) by physiological diplopia (when one is looking at one of the frames, the second have to be seen double in the background.

The little picture's motion (near frame 310) towards the nose, the large picture's light 305 is on, with the little picture's back motion (reverse) the little picture's light 314 is on. The patient never focuses on the light, the light is always in the background.

When step 614 has been completed to satisfaction of the professional then a reverse small picture step 616 is performed and STOP after this, there is the start of the small picture's reverse movement, while the patient is looking at the large frame (Relax).

Every time that one doesn't reach the required result, he can stop or do reverse while he is trying to see the little simple image or red letter, symbol or number, and see the physiological diplopia.

When the near frame is moving backwards, the patient is asked to stare on the rear frame and a taped vocal tape is activated. One non-limiting example of the taped message is "NOW RELAX. BLINKING GENTLY AND SMOOTHLY AND STARING FREELY. TURN YOUR EYES FROM SIDE TO SIDE, THEN IN A COMPLETE CIRCLE FROM LEFT TO RIGHT, AND BACKWARDS. LET YOUR EYES MUSCLES RELAX COMPLETELY!" This message may be played with background music or a short story.

It should be understood that the method taught herein may be used in any language. Furthermore any combination of music, sound, voice recording and other audio recordings may be used.

It should be understood that the method taught herein may be subject to many permutations and combinations, according to the patient being treated. For example, the same steps may be performed in the same way with 3D images, and thereafter without lens at all. Thereafter, in a more difficult exercise, the method may be performed with lenses or base-out prisms.

The methods of the present invention may be used to enhance the independence of a user, such as, but not limited to, training the user to perform other online tasks using a computer, tablet or cell phone, for example.

Figure 7:
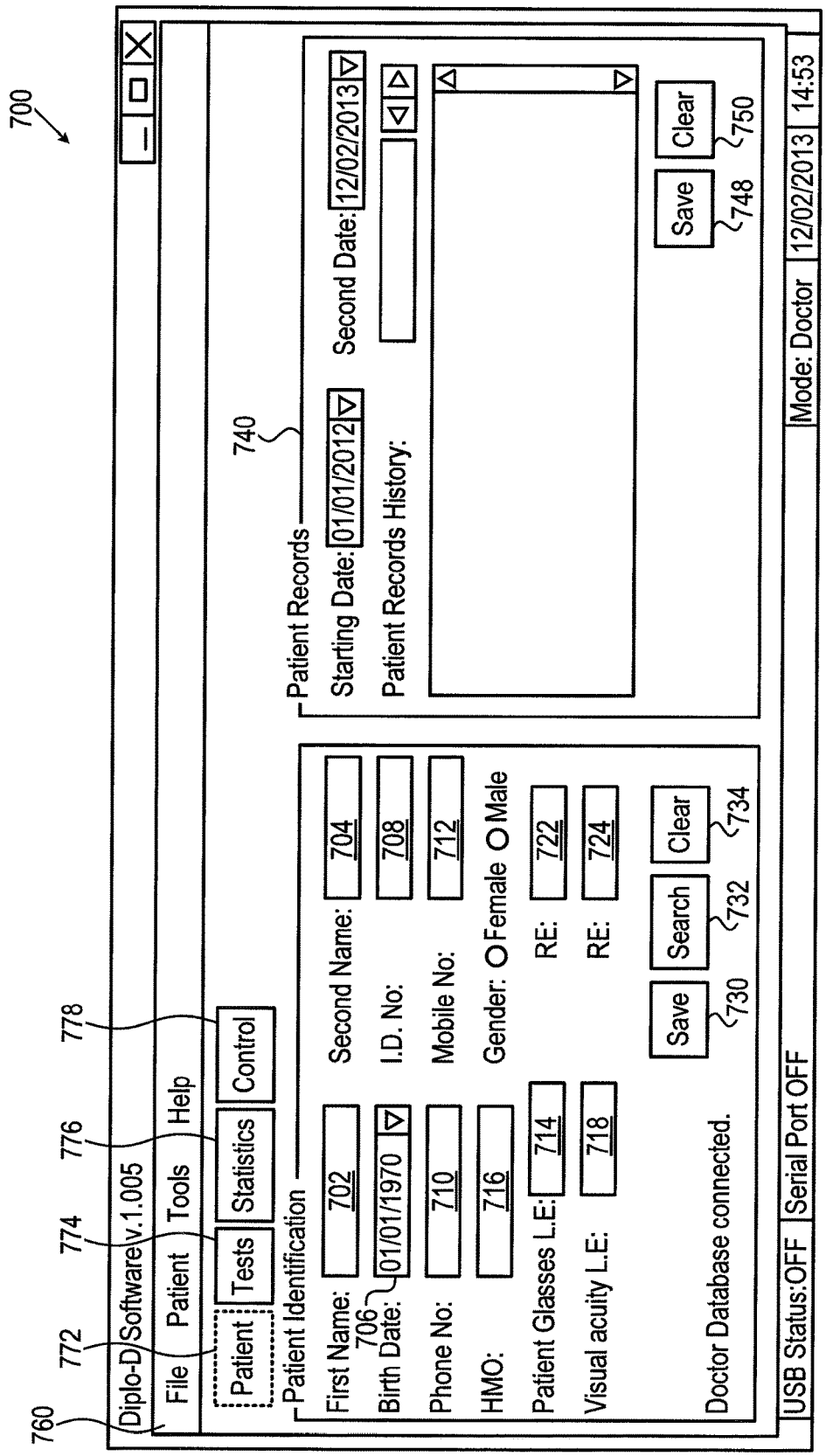
FIG. 7 is a simplified screen shot of a patient tracking record in the system of FIG. 1, in accordance with an embodiment of the present invention.

Reference is now made to FIG. 7, which is a simplified screen shot of a patient tracking record 700 in the system of FIG. 1, in accordance with an embodiment of the present invention. A health professional, such as a doctor typically accesses such a record in a professional environment in "doctor mode" only with a password. A patient may access his/her own record at home, for example, without any password. In doctor mode, the professional doctor fills in all the details about the patient in relevant labeled fields 702, 704, 706, 708, 710, 712, 722 and 724 on the left hand side of the screen. The left side data, includes, for example: patient identification: names, birth date, phone numbers, identity number, HMO (Health Maintenance Organization, gender, patient eyeglasses: right and left eye. data relating to visual acuity for right and left eyes.

Once the patient data has been entered, the doctor "clicks" on a "save" button 730. Additional buttons include "search" 732 and "clear" 734.

The right side of the screen includes an historic patient record 740 which fields such as a: start date 742 and stop date (treatment dates) 744, and patient records history 746.

Every time that these fields are updated, the doctor clicks on a save button or on a clear button 750 in the event of incorrect data entry.

When one wishes to retrieve a particular patient record, one can press the search 722 button and then to input only one of the patient details (name or id number) and click on "search 732 to retrieve the record from the memory.

The screenshot also comprises at least one toolbar 760. There are further tabs, such as patient 772, tests 774, statistics 774 and control 778, which appear in the screenshot.

Reference is now made to FIG. 8, which is another simplified screen shot 800 of a patient tracking record in the system of FIG. 1, in accordance with an embodiment of the present invention. Various test results appear when the tab test 774 is depressed. These may include:

Phoria 802 for near measure of the latent strabismus angle (in prismatic dioptries) in the near sight condition;

CNP 804: convergence near point: the nearest distance to the nose root one can see simple (or with both eyes together) while a target is approaching toward his eyes Stereoscopic vision 808 by Wirth Fly Stereo-test or other kind of stereo-test measured in seconds Worth 4 dots 806: binocular vision test, shows fusion (4 lights), or intermittent suppression (only 3 or 2 lights by intermittence), or 5 from time to time (intermittent diplopia)

Symptoms 810: there are at least 25 symptoms, as appearing in table 1 hereinbelow for the convergence insufficiency syndrome, every symptom has a number that the doctor write at this place for ex.: 6, 14=double vision, dizziness Adduction D' for near D' 812: it is the eyes muscles power in divergence in the near vision condition Speed 814: in values from 1 to 12: which is the speed of the little picture (near frame 310) while approaching the patient's eyes Last treatment level 816: from 1 to 5 (see the 5 levels of training with the device)

Adduction for near C' 818: it is the eyes muscles power in convergence in the near vision condition C/GL,S/GL 820: with or without glasses Tested before and after treatment 830: the patients are checked twice: before and after the treatment and the results are registered Then, the doctors clicks on save 840 or clear 842.

Tools and Export

When all the details are registered, the SD memory card is inserted into the computer and one clicks on tools and then: export (in the menu 760). It is checked to ensure that all the parameters are there and then the export button is clicked.

Tools and Import

After the patient has done his exercise with the same SD card into the optic device, we put back the card in the computer, click on tools and then import (in the menu), we check everything and click on import (button).

Figure 9:
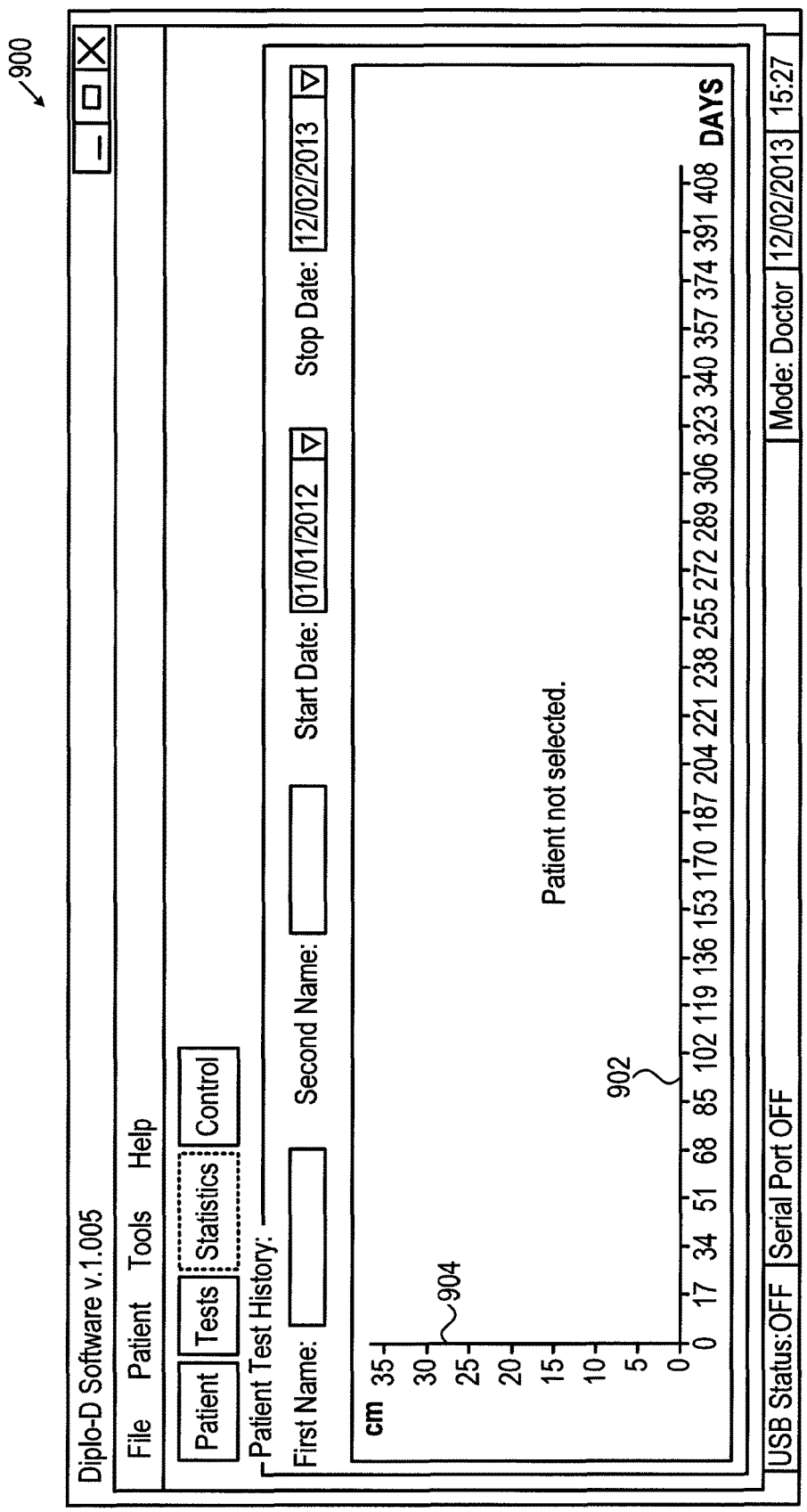
FIG. 9 is another simplified screen shot of a patient tracking record in the system of FIG. 1, in accordance with an embodiment of the present invention.

FIG. 9 is another simplified screen shot 900 of a patient tracking record in the system of FIG. 1, in accordance with an embodiment of the present invention. On X axis 902 the training days are recorded and on the Y axis 904 the performance in centimeters of the patient's eyes. We can choose the period we are interested to see with the arrows in the upper part of the screen: start date, stop date.

Figure 10:
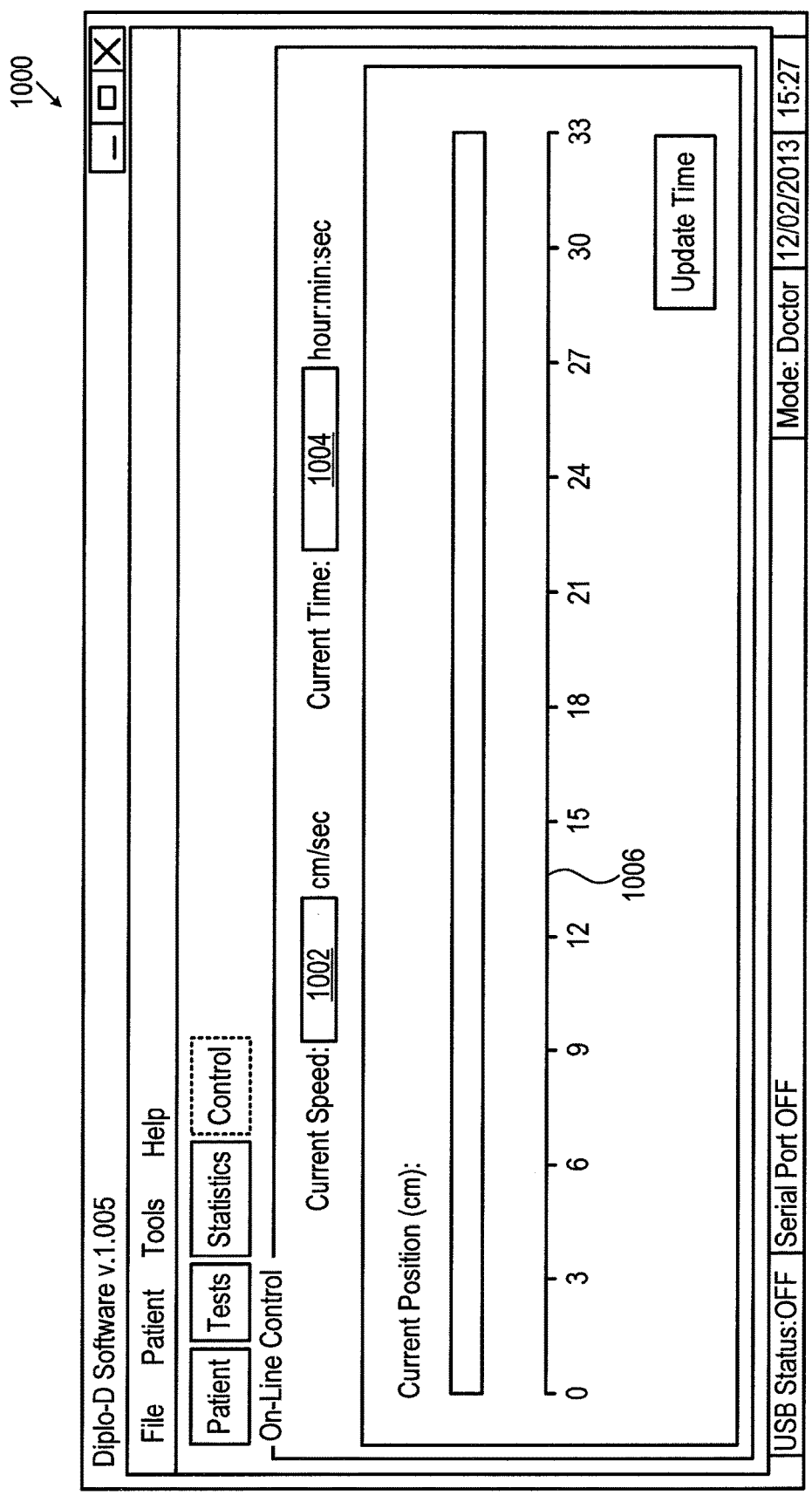
FIG. 10 is another simplified screenshot of real time tracking of the patient's current speed in the exercise, in accordance with an embodiment of the present invention.

FIG. 10 is another simplified screenshot 1000 of real time tracking of the patient's current speed in the exercise, in accordance with an embodiment of the present invention. Control is the follow up of the patient, when the optic device is connected to the computer by an USB cable, the doctor (or anyone who supervises the exercise) can see the workprocess online.in the upper part of this screen we can see the current speed 1002 in cm per sec., and the current time 1004, as well as the current position 1006.

According to some embodiments of the present invention, the systems and apparatus described herein are used to treat convergence insufficiency in a patient. A non-limiting list of some of the common symptoms in convergence insufficiency appear in Table 1 herein below. These symptoms are monitored over the period of treatment of several months and can be used to define qualitative and/or quantitative improvements/changes during the treatment period.

TABLE 1

Common Symptoms in Convergence Insufficiency

| No. | Symptom |
|---|---|
| 1 | Occasional blurred vision |
| 2 | Headaches |
| 3 | Problems in reading |
| 4 | Eye fatigue |
| 5 | Blurred reading |
| 6 | Seeing double |
| 7 | Difficulty in focusing |
| 8 | Stabbing pains in eyes |
| 9 | Eye pain |
| 10 | Blinking |
| 11 | Occasional loss of tracking |
| 12 | Bright light blindness |
| 13 | Rubbing of eyes |
| 14 | Dizziness |
| 15 | Burning eyes |
| 16 | Heavy eyes |
| 17 | Tear drops |
| 18 | Eyes pressure feeling |
| 19 | Problems in writing down from black/whiteboard |
| 20 | Lack of control of eye closure |
| 21 | Does not get used to reading glasses |
| 22 | General fatigue |
| 23 | Closes one eye when reading |
| 24 | Red eyes |
| 25 | Holds head in slanted position |
| 26 | Other, such as difficulties at school and difficulties on a computer |

According to some further embodiments of the present invention, the systems and apparatus described herein are used to treat for eye training in a patient. There are several accessories, which are used in a number of different stages. One non-limiting example appears in Table 2 herein below.

The systems of the present invention may be built to any suitable size and dimensions, such as 30 cm×30 cm×70 cm. These exemplary dimensions should not be deemed limiting.

It should also be understood that the systems of the present invention may be activated by guests and host users in combinations other than those described herein.

TABLE 2

Stages of Eye training and use of accessories therein.

| STAGE NUMBER | LENSES | COLOR FILTER* | LIGHTS |
|---|---|---|---|
| STAGE ONE | −3 LENSES | +COLOR FILTER | +LIGHTS |
| STAGE TWO | −3 LENSES | NO COLOR FILTER | +LIGHTS |
| STAGE THREE | NO LENSES | NO COLOR FILTER | +LIGHTS |
| STAGE FOUR | NO LENSES | NO COLOR FILTER | NO LIGHTS |
| STAGE FIVE | +3 LENSES or addition of base-out prism | NO COLOR FILTER | NO LIGHTS |

*According to some embodiments, color filters may be replaced by Polaroid lenses. On the other hand, in some occurrences of 3D tests, Polaroid lenses or color filters are not required.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A computerized operator-controlled optical system for tracking eye exercises of a patient, the system comprising:
   a) an optical tracking device adapted to allow an operator to track eye exercises of a patient;
   b) a patient-activated apparatus for performing eye exercises of both eyes together, the patient activated apparatus comprising:
      i. a near frame;
      ii. a far frame;
      iii. a rail upon which said near frame and said far frame are vertically disposed; and
      iv. patient activated controller buttons for moving at least one of said near frame and said far frame along said rail and
   c) a processor adapted to receive data from said optical tracking device and from said patient-activated apparatus thereby providing said operator with at least one indication of said eye exercises of said patient over time,
   wherein said patient a patient-activated apparatus further comprises:
      a. an ocular apparatus disposed at a front end of said patient-activated apparatus, said ocular apparatus comprising:
         i. two viewing apertures, each disposed to be located in front of one of said patient's eye;
         ii. each of said viewing apertures adapted to receive at least one of:
            a. an optical lens;
            b. an optical filter; and
            c. a prismatic lens,
   wherein said first and said second picture are test images selected from at least one of a picture, a photo, an alphanumeric symbol and at least one colored shape, and
   wherein said patient-activated apparatus further comprises an audio feedback element for generating, during said eye exercises, an audio signal whose characteristics are indicative of a distance of one of said test images from said viewing apertures.

2. A computerized operator-controlled optical system according to claim 1, wherein said patient activated apparatus further comprises a motor in electrical connection with a motor controller, said motor controller is connected to an adjustable speed control for moving said near frame along said rail at an adjustable speed.

3. A computerized operator-controlled optical system according to claim 2, wherein said near frame is adapted to hold at least one of a centrally placed light, a first picture and a first alphanumeric character.

4. A computerized operator-controlled optical system according to claim 3, wherein said far frame is adapted to hold at least one of a second centrally placed light, a second picture and a second alphanumeric character.

5. A computerized operator-controlled optical system according to claim 1, further comprising an electronic apparatus adapted to download said data to a memory in said system.

6. A computerized operator-controlled optical system according to claim 1, further comprising software readable by said processor, wherein said software is adapted to form patient records over time.

7. A computerized operator-controlled optical system according to claim 1, wherein said optical tracking device is a video camera.

8. A computerized operator-controlled optical system according to claim 7, wherein said video camera is adapted to capture multiple images of each said patient's eyes.

9. A computerized operator-controlled optical system according to claim 1, wherein said patient-activated apparatus further comprises a housing comprising a lid a base and a support, said base adapted to house said near frame, said far frame and said rail.

10. A computerized operator-controlled optical system according to claim 1, wherein said system is constructed and configured to improve eye fusion deficiencies selected from convergence insufficiency, divergence excess, intermittent strabismus and combinations thereof.

11. A computerized operator-controlled optical system according to claim 1, wherein said audio feedback signal characteristics are selected from a frequency thereof and a pulse repetition rate.

* * * * *